United States Patent
Hendrix et al.

(10) Patent No.: US 6,511,706 B1
(45) Date of Patent: Jan. 28, 2003

(54) MOCVD OF SBT USING TETRAHYDROFURAN-BASED SOLVENT SYSTEM FOR PRECURSOR DELIVERY

(75) Inventors: Bryan C. Hendrix, Danbury, CT (US); Thomas H. Baum, New Fairfield, CT (US); Debra A. Desrochers-Christos, Monroe, CT (US); Jeffrey F. Roeder, Brookfield, CT (US); Witold Paw, New Fairfield, CT (US)

(73) Assignee: Advanced Technology Materials, Inc., Danbury, CT (US)

(*) Notice: Subject to any disclaimer, the term of this patent is extended or adjusted under 35 U.S.C. 154(b) by 0 days.

(21) Appl. No.: 09/441,694

(22) Filed: Nov. 16, 1999

Related U.S. Application Data

(63) Continuation-in-part of application No. 09/224,614, filed on Dec. 31, 1998, now Pat. No. 6,111,124, which is a continuation-in-part of application No. 08/960,915, filed on Oct. 30, 1997, now Pat. No. 5,859,274, application No. 09/441,694, which is a continuation-in-part of application No. 08/484,654, filed on Jun. 7, 1995, now Pat. No. 6,110,529, which is a continuation-in-part of application No. 08/414,504, filed on Mar. 31, 1995, now Pat. No. 5,820,664, which is a continuation-in-part of application No. 08/280,143, filed on Jul. 25, 1994, now Pat. No. 5,536,323, which is a continuation of application No. 07/927,134, filed on Aug. 7, 1992, now abandoned, which is a continuation-in-part of application No. 07/807,807, filed on Dec. 13, 1991, now Pat. No. 5,204,314, which is a continuation of application No. 07/549,389, filed on Jul. 6, 1990, now abandoned, which is a continuation-in-part of application No. 08/181,800, filed on Jan. 18, 1994, now Pat. No. 5,453,494, which is a continuation-in-part of application No. 07/918,141, filed on Jul. 22, 1992, now Pat. No. 5,280,012, which is a continuation of application No. 07/615,303, filed on Nov. 19, 1990, now abandoned, which is a division of application No. 07/581,631, filed on Sep. 12, 1990, now Pat. No. 5,225,561, which is a continuation-in-part of application No. 07/549,389, filed on Sep. 12, 1990, now abandoned.

(51) Int. Cl.$^7$ .............................................. C23C 16/40
(52) U.S. Cl. ............. 427/255.32; 427/907; 106/287.18; 106/287.2; 106/287.21; 106/287.23
(58) Field of Search ........................ 106/287.18, 287.2, 106/287.21, 287.3, 287.23, 311; 427/255.32, 901

(56) References Cited

U.S. PATENT DOCUMENTS

| | | | |
|---|---|---|---|
| 4,975,299 A | | 12/1990 | Mir et al. |
| 5,204,314 A | | 4/1993 | Kirlin et al. |
| 5,225,561 A | | 7/1993 | Kirlin et al. |
| 5,280,012 A | | 1/1994 | Kirlin et al. |
| 5,304,533 A | | 4/1994 | Kobayashi et al. |
| 5,372,850 A | | 12/1994 | Uchikawa et al. |
| 5,453,494 A | * | 9/1995 | Kirlin et al. |
| 5,478,610 A | * | 12/1995 | Desu et al. |
| 5,536,323 A | | 7/1996 | Kirlin et al. |
| 5,555,154 A | | 9/1996 | Uchikawa et al. |
| 5,629,229 A | | 5/1997 | Si et al. |
| 5,677,002 A | * | 10/1997 | Kirlin et al. |
| 5,679,815 A | | 10/1997 | Kirlin et al. |
| 5,700,400 A | | 12/1997 | Ikai et al. |
| 5,820,664 A | | 10/1998 | Gardiner et al. |
| 5,859,274 A | | 1/1999 | Baum et al. |
| 5,900,279 A | | 5/1999 | Hideaki et al. |
| 5,916,359 A | | 6/1999 | Baum et al. |
| 5,919,522 A | | 7/1999 | Baum et al. |
| 5,997,637 A | | 12/1999 | Ikai et al. |
| 6,110,529 A | | 8/2000 | Gardiner et al. |
| 6,111,124 A | * | 8/2000 | Baum et al. |

FOREIGN PATENT DOCUMENTS

JP       07268634       10/1995

OTHER PUBLICATIONS

Ami et al., Mat. Res. Soc. Symp. Proc. vol. 415 (1996), pp. 195–200 (no month).*

Takaaki Kawahara, Mikio Yamamuka, Akimisa Yuuki and Kouichi Ono, Jpn., J. Appl. Phys., vol. 34, (1995), Part 1, No. 9B, pp. 5077–5082 (no month).

* cited by examiner

Primary Examiner—Timothy Meeks
(74) Attorney, Agent, or Firm—Margaret Chappuis

(57) ABSTRACT

A precursor composition useful for liquid delivery MOCVD, including SBT precursors dissolved in a solvent system containing tetrahydrofuran. The associated liquid delivery MOCVD process may be carried out with vaporization of the precursor composition on a porous vaporization element having an average pore diameter in the range of from about 50 to about 200 micrometers, with the resultant precursor vapor being admixed with a carrier gas to achieve high efficiency formation of SBT films.

41 Claims, 4 Drawing Sheets

MOCVD OF SBT USING TETRAHYDROFURAN-BASED SOLVENT SYSTEM FOR PRECURSOR DELIVERY

CROSS REFERENCE TO RELATED U.S. APPLICATIONS

This application is a continuation-in-part of U.S. patent application Ser. No. 09/224,614 filed Dec. 31, 1998 in the names of Thomas H. Baum and Raymond H. Dubois, entitled "LEWIS BASE ADDUCTS OF ANHYDROUS MONONUCLEAR TRIS(β-DIKETONATE) BISMUTH COMPOSITIONS FOR DEPOSITION OF BISMUTH-CONTAINING FILMS, AND METHOD OF MAKING THE SAME", issued as U.S. Pat. No. 6,111,124 on Aug. 29, 2000 which is a continuation-in-part of Ser. No. 08/960,915, filed Oct. 30, 1997, now U.S. Pat. No. 5,859,274. This application is also a continuation-in-part of Ser. No. 08/484,654, filed Jun. 7, 1995, now U.S. Pat. No. 6,110,529, which is a continuation-in-part of Ser. No. 08/414,504, filed Mar. 31, 1995, now U.S. Pat. No. 5,820,664, which is a continuation-in-part of Ser. No. 08/280,143, filed Jul. 25, 1994, now U.S. Pat. No. 5,536,323, which is a continuation of Ser. No. 07/927,134, filed Aug. 7, 1992, now abandoned, which is a continuation-in-part of Ser. No. 07/807,807, filed Dec. 13, 1991, now U.S. Pat. No. 5,204,314, which is a continuation of Ser. No. 07/549,389, filed Jul. 6, 1990, now abandoned, which is a continuation-in-part of 08/181,800, filed Jan. 18, 1994, now U.S. Pat. No. 5,453,494, which is a continuation-in-part of Ser. No. 07/918,141, filed Jul. 22, 1992, now U.S. Pat. No. 5,280,012, which is a continuation of Ser. No. 07/615,303, filed Nov. 19, 1990, now abandoned, which is a divisional of Ser. No. 07/581,631, filed Sep. 12, 1990, now U.S. Pat. No. 5,225,561, which is a continuation-in-part of Ser. No. 07/549,389, now abandoned.

BACKGROUND OF THE INVENTION

1. Field of the Invention

This invention relates to metalorganic chemical vapor deposition (MOCVD) of strontium bismuth tantalate and in particular to a tetrahydrofuran-based solvent system for precursor delivery for MOCVD of such material

2. Description of the Related Art

Liquid delivery MOCVD is the preferred method for depositing thin films of ferroelectric materials because of the ability to carefully control composition and deposit conformal films of high density. In such processes a solution or suspension of precursors (metalorganic source reagents for the respective metal components of the product film material) is vaporized, preferably at high rate by "flash vaporization" techniques to produce a corresponding precursor vapor which may be mixed with carrier and/or additive gases (e.g., oxygen-containing gas, inert gases such as argon, helium, etc., co-reactive gases, diluents, etc.) to form a vapor mixture. The vapor mixture then is flowed to a deposition zone where the precursor mixture is contacted with a substrate at elevated temperature to effect deposition from the vapor phase onto the substrate of a desired material. MOCVD of $SrBi_2Ta_2O_9$ (SBT) and related materials use precursors that are chemically compatible in solution for long periods of time and also have similar decomposition characteristics vis-à-vis one another in the MOCVD process. $Sr(thd)_2$-LBA, $Bi(thd)_3$, and $Ta(O-i-Pr)_4(thd)$ (where thd stands for 2,2,7,7-tetramethyl-3,5-heptanedionato, LBA stands for a Lewis base adduct and O-i-Pr stands for isopropoxide) provide a preferred combination of precursors for such purpose. Precursors for deposition of SBT and other ferroelectric materials, and their use in liquid delivery MOCVD formation of high quality product films, are more fully described in U.S. patent application Ser. No. 08/960,915 filed Oct. 30, 1997 in the names of Thomas H. Baum, et al., now issued as U.S. Pat. No. 5,859,274, and U.S. patent application Ser. No. 08/976,087 filed Nov. 20, 1997 in the names of Frank S. Hintermaier, et al.

The best previously known solvent system for this precursor suite (of $Sr(thd)_2$-LBA, $Bi(thd)_3$, and $Ta(O-i-Pr)_4(thd)$) consisted of alkanes and in particular a mixture of octane, decane, with an excess of the LBA of the strontium precursor, $Sr(thd)_2$. In particular, a ratio of 5 parts octane, 4 parts decane, and 1 part LBA was found to maintain the precursors in a stable condition and deliver them reliably to a flash vaporization equipment. Solvent compositions of such type are more fully described in U.S. patent application Ser. No. 08/975,372 filed Nov. 20, 1997 in the names of Thomas H. Baum, et al., now issued as U.S. Pat. No. 5,916,359.

However, the alkane-based solvents have limited solubility of the aforementioned SBT precursors, especially for the $Sr(thd)_2$, which only dissolves to about 0.2 M in a 5:4:1 mixture of octane:decane:pmdeta. This limited solubility characteristic of the solvent composition has disadvantages for liquid delivery vaporization and the subsequent deposition process. During vaporization, wherein the precursor solution typically is flowed through a liquid delivery tube to a heated surface, the molarity of the precursor solution must remain significantly below the solubility limit to prevent precipitation of solid metalorganic particles from the solution, which would otherwise occur as solvent boils off in the liquid delivery tube, and which would lead to clogging of the liquid delivery tube. In addition, low solution molarity requires the vaporization of more solvent in order to deliver the same amount of precursor to the process. This creates undue requirements for the supply of heat to the metalorganics in the vaporizer, since more heat must then be provided to volatilize the additional solvent that is present.

The deposition process itself also is adversely affected by low molarity solutions. By way of example, film growth rates were limited to 3–4 nanometers per minute (nm/min) in a prototype MOCVD reactor delivering a 0.30M solution at a rate of 0.2 ml/min. Growth rates should be 2–10 times higher than this level in order to meet the requirements of a "manufacturable process." In addition, limiting the rate of delivery of precursor to the substrate surface makes it more difficult to push the process into a surface kinetic-controlled growth regime where conformality to non-planar structures is improved, relative to film formation processes operating outside of such regime.

It would therefore be an advance in the art to provide a solvent medium for liquid delivery MOCVD of precursor compositions such as SBT, which overcome the aforementioned difficulties.

SUMMARY OF THE INVENTION

The present invention relates to a precursor composition that is usefully employed for liquid delivery MOCVD applications, e.g., for SBT, doped SBT and other ferroelectric precursors.

The invention relates in one aspect to a precursor composition useful for liquid delivery MOCVD, comprising SBT precursors dissolved in a solvent system containing tetrahydrofuran (THF). The solvent system may for example be constituted in major portion by THF, or it may be constituted solely by THF, or it may consist essentially of THF. In such precursor composition, $Sr(thd)_2(THF)_4$ is a preferred chemical species for the introduction of Sr.

The invention relates in another aspect to a precursor composition useful for liquid delivery MOCVD comprising SBT precursors dissolved in a solvent system comprising 90–99 parts by volume tetrahydrofuran and 1–10 parts by volume Lewis base ligand (LBA). In such composition, $Sr(thd)_2(LBA)_x$, wherein x is from 1 to 4, is a preferred chemical species for the introduction of Sr.

The invention relates in another aspect to a precursor composition useful for liquid delivery MOCVD, comprising SBT precursors and a dopant precursor, e.g., niobium beta-diketonate, dissolved in a solvent system including tetrahydrofuran. In such composition, $Sr(thd)_2(THF)_4$ is a preferred chemical species for the introduction of Sr.

The invention relates in a still further aspect to a precursor composition useful for liquid delivery MOCVD, comprising SBT precursors and a dopant precursor, e.g., niobium beta-diketonate, dissolved in a solvent system comprising 90–99 parts by volume tetrahydrofuran and 1–10 parts by volume LBA. In such composition, $Sr(thd)_2(LBA)_x$ wherein x is from 1 to 4, is a preferred chemical species for the introduction of Sr.

Another aspect of the invention relates to an SBT precursor composition comprising SBT precursors dissolved in a solvent medium including tetrahydrofuran, e.g., a solvent medium consisting essentially of tetrahydrofuran, with such SBT precursor composition having a boiling point at 1 atmosphere pressure of about 66° C. The SBT precursors of such composition desirably comprise $Sr(thd)_2(THF)_4$ as a preferred chemical species for the introduction of Sr due to its high solubility and low melting point.

Another aspect of the invention relates to an SBT precursor composition comprising SBT precursors and a dopant component, e.g., a dopant precursor, dissolved in a solvent medium containing tetrahydrofuran, having a boiling point at 1 atmosphere pressure of about 66° C. The SBT precursors of such composition desirably comprise $Sr(thd)_2(THF)_4$ as a preferred chemical species for the introduction of Sr due to its high solubility and low melting point.

A further aspect of the invention relates to a method of forming SBT material on a substrate, comprising:

providing a precursor composition for SBT;

volatilizing the precursor composition to yield a precursor vapor; and contacting the precursor vapor with the substrate to deposit SBT thereon;

wherein the precursor composition comprises SBT precursors dissolved in a solvent medium containing tetrahydrofuran. The SBT precursors of such composition desirably comprise $Sr(thd)_2(THF)_4$ as a preferred chemical species for the introduction of Sr due to its high solubility and low melting point.

A further aspect of the invention relates to a method of forming doped SBT material on a substrate, comprising:

providing a precursor composition for doped SBT;

volatilizing the precursor composition to yield a precursor vapor; and contacting the precursor vapor with a substrate to deposit doped SBT thereon.

In such method, the precursor composition advantageously comprises SBT precursors and a dopant precursor, e.g., niobium beta-diketonate, dissolved in a solvent medium containing tetrahydrofuran, wherein $Sr(thd)_2(THF)_4$ is a preferred chemical species for the introduction of Sr due to its low melting point and high solubility in THF.

A further aspect of the invention relates to a method of forming SBT material on a substrate, comprising:

providing a precursor composition for SBT;

volatilizing the precursor composition to yield a precursor vapor; and contacting the precursor vapor with a substrate to deposit SBT thereon, wherein the precursor composition comprises SBT precursors dissolved in a solvent system comprising 90–99 parts by volume tetrahydrofuran and 1–10 parts by volume LBA. In such composition, $Sr(thd)_2(LBA)_x$, wherein x is from 1 to 4, is a preferred chemical species for the introduction of Sr.

In another aspect, the invention relates to a method of forming an SBT film on a substrate, comprising liquid delivery MOCVD using a precursor composition comprising SBT precursors dissolved in a solvent medium containing tetrahydrofuran. In such composition, $Sr(thd)_2(THF)_4$ is a preferred chemical species for the introduction of Sr due to its low melting point and high solubility in THF.

In a further aspect, the invention relates to a method of forming a doped SBT film, e.g., niobium doped SBT, on a substrate, comprising liquid delivery MOCVD using a precursor composition comprising SBT precursors and a dopant precursor dissolved in a solvent medium containing tetrahydrofuran. In such composition, $Sr(thd)_2(THF)_4$ is a preferred chemical species for the introduction of Sr due to its low melting point and high solubility in THF.

A still further aspect of the invention relates to a method of forming an SBT film on a substrate, comprising liquid delivery MOCVD using a precursor composition comprising SBT precursors dissolved in a solvent system comprising tetrahydrofuran and a Lewis base ligand. In such composition, $Sr(thd)_2(LBA)_x$ wherein x is from 1 to 4, is a preferred chemical species for the introduction of Sr.

The aforementioned precursor compositions of the present invention provide preferred combinations of precursors that are chemically compatible in solution for extended periods of time and have similar decomposition characteristics vis-à-vis one another in the MOCVD process for deposition of SBT and other ferroelectric materials.

Other objects, features and advantages of the invention will be more fully apparent from the ensuing disclosure and appended claims.

DETAILED DESCRIPTION OF THE INVENTION AND PREFERRED EMBODIMENTS THEREOF

Figure 1:
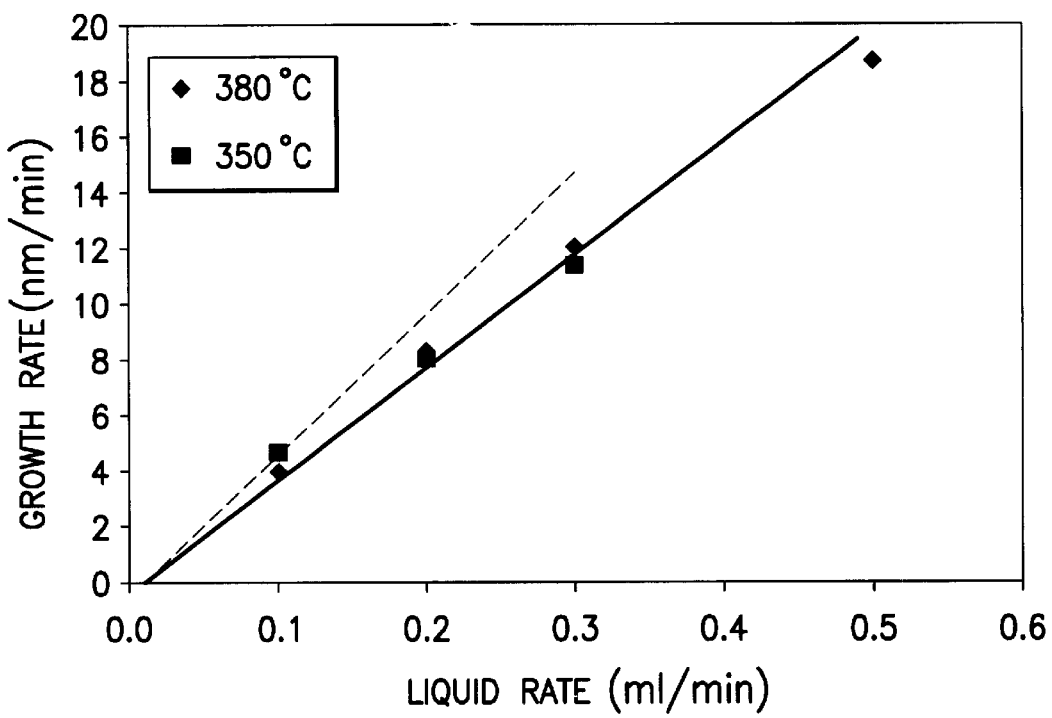
FIG. 1 is a graph of growth rate as a function of liquid delivery rate for 9 torr processes at 380° C. and at 350° C. using 0.2 M solution (total precursor molarity) in 5:4:1 octane:decane:pmdeta (pentamethyldiethylenetriamine), wherein lines indicating a linear proportional increase in growth rate are shown for comparison to the measured increase in growth rate.

The disclosure of the following United States patents and patent applications, which are commonly owned by assignee of the present application, are hereby incorporated herein by reference in their entireties:

U.S. patent application Ser. No. 08/835,768 filed Apr. 8, 1997 in the names of Thomas H. Baum, et al., which was issued as U.S. Pat. No. 5,919,522 on Jul. 6, 1999;

U.S. patent application Ser. No. 08/484,654 filed Jun. 7, 1995 in the names of Robin A. Gardiner et al., which was issued as U.S. Pat. No. 6,110,529 on Aug. 29, 2000;

U.S. patent application Ser. No. 08/307,316 filed Sep. 16, 1994 in the names of Peter S. Kirlin et al., which was issued as U.S. Pat. No. 5,679,815 on Oct. 21, 1997;

U.S. patent application Ser. No. 08/453,380 filed May 30, 1995 in the names of Peter S. Kirlin et al., which was issued as U.S. Pat. No. 5,677,002 on Oct. 14, 1997;

U.S. patent application Ser. No. 08/414,504 filed Mar. 31, 1995 in the names of Robin A. Gardiner et al., which was issued as U.S. Pat. No. 5,820,664 on Oct. 13, 1998;

U.S. patent application Ser. No. 08/280,143 filed Jul. 25, 1994, in the names of Peter S. Kirlin et al., which was issued as U.S. Pat. No. 5,536,323 on Jul. 16, 1996;

U.S. patent application Ser. No. 07/927,134, filed Aug. 7, 1992 in the same names, which was abandoned;

U.S. patent application Ser. No. 07/807,807, filed Dec. 13, 1991 in the names of Peter S. Kirlin, et al., which was issued as U.S. Pat. No. 5,204,314 on Apr. 20, 1993;

U.S. patent application Ser. No. 08/181,800 filed Jan. 15, 1994 in the names of Peter S. Kirlin, et al., and issued as U.S. Pat. No. 5,453,494 on Sep. 26, 1995;

U.S. application Ser. No. 07/918,141 filed Jul. 22, 1992 in the names of Peter S. Kirlin, et al., and issued as U.S. Pat. No. 5,453,494;

U.S. patent application Ser. No. 07/615,303 filed Nov. 19, 1990 in the names of Peter S. Kirlin, et al., which was abandoned;

U.S. patent application Ser. No. 07/518,631 filed Sep. 12, 1990 in the names of Peter S. Kirlin, et al., and issued Jul. 6, 1993 as U.S. Pat. No. 5,225,561;

U.S. patent application Ser. No. 07/549,389 filed Jul. 6, 1990 in the names of Peter S. Kirlin, et al., which was abandoned;

U.S. patent application Ser. No. 08/975,372, filed Nov. 20, 1997 in the names of Thomas H. Baum, et al., which was issued as U.S. Pat. No. 5,916,359 on Jun. 29, 1999;

U.S. patent application Ser. No. 08/960,915 filed Oct. 30, 1997 in the names of Thomas H. Baum, et al., which was issued as U.S. Pat. No. 5,859,274 on Jun. 29, 1999; and U.S. patent application Ser. No. 08/975,087 filed Nov. 20, 1997 in the names of Frank S. Hintermaier, et al, which is currently pending.

The present invention is based on the discovery that a tetrahydrofuran solvent system or solvent systems comprising tetrahydrofuran, when used for the liquid delivery MOCVD of SBT, has high solubility of all precursor components and no undesired chemical interactions. Further, Sr(thd)$_2$(THF)$_4$ is a preferred chemical species for the introduction of Sr (as a component into the product film deposited on the substrate), in consequence of its high solubility in THF and its low melting point. These characteristics significantly aid the "flash vaporization" of the precursor and transport of the chemical mixture to the chemical vapor deposition chamber.

For example, as applied to the MOCVD of SBT using the aforementioned preferred precursor combination of Sr(thd)$_2$, Bi(thd)$_3$, and Ta(O-i-Pr)$_4$(thd), it was found that the tetrahydrofuran coordinates to the Sr(thd)$_2$ component of the precursor composition, yielding a precursor composition composition comprising Sr(thd)$_2$-LBA, wherein LBA is THF, that is in the liquid phase at low temperature (where Sr(thd)$_2$(THF)$_4$ melts at temperatures >28° C).

Further, it is expected that tetrahydrofuran coordinates to the Bi(thd)$_3$ component to produce a Bi(thd)$_3$-(LBA)$_x$ species, wherein LBA is THF and x has a value of 1 to 4, consistent with the discovery that Lewis base ligands form adducts with Bi(thd)$_3$ as more fully described in copending U.S. patent application Ser. No. 09/224,614 filed Dec. 31, 1998 in the names of Thomas H. Baum, et al., now allowed.

Vaporization of such SBT precursor composition, comprising SBT precursors dissolved in tetrahydrofuran, at 0.3 M total solution molarity and a flow rate of 0.30 ml/min gave vaporizer mean time to service (MTS) similar to a corresponding precursor composition in 5:4:1 octane:decane:pmdeta (ratio by volume). The mean time to service is a measure of the extent of premature decomposition of the precursors in the vaporizer, the occurrence of side reactions in the vaporizer, and unwanted deposition of solids and viscous byproducts in the vaporizer. Thus, the "cleaner" the vaporization operation in the vaporizer zone, the longer will be the MTS for the system. It is highly desirable to achieve MTS values as high as possible (i.e., the longest possible time between maintenance events for the vaporizer), since this maximizes on-stream time and equipment utility, and minimizes operating costs of the liquid vaporization MOCVD system.

The above-noted results achieved by the tetrahydrofuran solvent compositions for the MOCVD of SBT, viz., vaporization of the aforementioned SBT precursors in tetrahydrofuran solution at 0.3 total solution molarity and 0.30 ml/min yielding vaporizer MTS values greater than the MTS for use of 5:4:1 octane:decane:pmdeta solvent compositions for the same SBT precursors, indicating that there are positive effects from the solvent system change and that vaporizer MTS is being primarily controlled by the precursors identities and solvents utilized. Despite the lower boiling point of the tetrahydrofuran solvent, there was surprisingly and unexpectedly no evidence of problems with precipitation from solvent boil-off in the delivery tube. These effects were primarily correlated with $Sr(thd)_2(THF)_4$, due to its high solubility and low melting point, as the preferred chemical species for the introduction and vaporization of Sr.

In addition, significantly improved vaporizer maintenance times were obtained with the tetrahydrofuran precursor compositions of the invention when the carrier gas was changed from argon to helium, and the average pore size of the vaporizer element was increased from a nominal 40 micrometers to nominal 100 micrometers.

The tetrahydrofuran-based precursor compositions of the present invention may be usefully employed for MOCVD of SBT and doped SBT using the aforementioned preferred precursors of $Sr(thd)_2$, $Bi(thd)_3$ and $Ta(O-i-Pr)_4(thd)$ at a total solution molarity in the range of from about 0.2 M to about 0.6 M.

The invention therefore contemplates a solvent composition that is unexpectedly superior for liquid delivery of precursors for SBT, such as the preferred $Sr(thd)_2$, $Bi(thd)_3$, and $Ta(O-i-Pr)_4(thd)$ precursors, that is readily formulated and permits high delivery rates and high growth rates to be achieved which provide a "manufacturable process" for thin film deposition of SBT by liquid delivery MOCVD techniques.

The invention further contemplates a solvent composition for liquid delivery of precursors for doped SBT, such as the preferred $Sr(thd)_2$, $Bi(thd)_3$ and $Ta(O-i-Pr)_4(thd)$ precursors as well as a dopant precursor, such as $Nb(O-i-Pr)_4(thd)$, that is readily formulated and permits high delivery rates and high growth rates to be achieved which provide a "manufacturable process" for thin film deposition of doped SBT by liquid delivery MOCVD techniques.

In the precursor composition of the invention, the Sr and Bi components may be beta-diketonates, such as the aforementioned "thd" beta-diketonate ligand. In tetrahydrofuran solution, the tetrahydrofuran coordinatively complexes with the beta-diketonate compounds to form an adduct.

In the precursor composition of the invention, the Ta component and the dopant component, e.g., Nb, may be beta-diketonates, such as the aforementioned "thd" beta-diketonate ligand. In particular, the precursor composition may for example comprise $Ta(O-i-Pr)_4(thd)$ and $Nb(O-i-Pr)_4(thd)$, respectively.

The β-diketonate ligand in the respective precursor components may be of any suitable type. Illustrative species and their notational abbreviations include: acac=acetylacetonate, more specifically 2,4-pentane dionate; hfacac (or hfac)=hexafluoroacetylacetonate, more specifically 1,1,1,5,5,5-hexafluoro-2,4-pentanedionate; tfacac (or tfac)=trifluoroacetylacetonate, more specifically 1,1,1-trifluoro-2,4-pentanedionate; thd=tetramethylheptanedionate, and more specifically 2,2,6,6-tetramethyl-3,5-heptanedionate; fod=fluorodimethyloctanedionate, more specifically 1,1,1,2,2,3,3-heptafluoro-7,7-dimethyl-4,6-octanedionate; tod=trimethyloctanedionate, more specifically 2,2,7-trimethyl-3,5-octanedionate; and hfod=heptafluoro-dimethyloctanedionate. The corresponding β-thioketonate ligands may also be used and are identified consistently with the foregoing β-diketonate ligand notation, by prefixation of "s" to the corresponding β-diketonate ligand, e.g., shfac, sthd, etc. Thus the β-diketonate ligands employed in metal source complexes of the present invention may usefully include acac, thd, fod, hfod, tfacac, and hfacac, and their corresponding thio analogs. Preferred THF adducts of the invention include Bi tris (2,2,6,6-tetramethyl-3,5-heptanedionate) and Sr bis (2,2,6,6-tetramethyl-3,5-heptanedionate).

In the precursor composition of the present invention, the THF ligands stabilize the mononuclear form of the precursor, and satisfy the coordination requirements of the metal center, thereby increasing the solubility and the volatility of the resultant complexes. While THF does not bind strongly and will readily dissociate upon heating or under vacuum from the complex, when the SBT beta-diketonate precursors of the invention are utilized in a solution of THF for liquid delivery chemical vapor deposition, the excess THF used as solvent effectively shifts the equilibrium to favor the THF adducted species. Such equilibrium shift thereby limits the loss or liberation of THF from the complex, so that the complex remains storage stable in the liquid solution, remains in the mononuclear form, remains exceedingly soluble and remains a low melting species. However, $Sr(thd)_2(THF)_4$ is readily volatilized and decomposed under chemical vapor deposition conditions to incorporate Sr into the SBT films.

The preferred precursor composition of the present invention, $Sr(thd)_2(THF)_4$, $Bi(thd)_3$ and $Ta(O-i-Pr)_4(thd)$ dissolved in tetrahydrofuran, provides a preferred combination of precursors that are chemically compatible in solution for long periods of time and also have similar decomposition characteristics vis-à-vis one another in the MOCVD process.

The use of tetrahydrofuran in accordance with the present invention overcomes the deficiencies of the prior art vaporization approach of chelating the metal β-diketonate with ligands containing many donor atoms, such as crown ethers or lariat polyethers, to fulfill the coordination sphere. Such prior art vaporization approach, while providing some improvement in stability relative to the metal β-diketonate per se, does not fully resolve the solubility and melting point depression issues achieved in the present invention. The precursor composition of the present invention overcomes these deficiencies by providing SBT beta-diketonate precursor complexes from which the THF ligands such as $Sr(thd)_2(THF)_4$, and can be readily adapted to liquid delivery chemical vapor deposition conditions.

The THF adducted complexes may be readily obtained by cooling of the THF solutions of the corresponding metal β-diketonate, e.g., of Bi and/or Sr. The resulting solid complexes recovered from the THF solution are crystalline solids that have unusually low melting points and high solubilities in THF at room temperature (25° C.).

The compositions of the invention and hereafter claimed may selectively and alternatively comprise, consist or consist essentially of any of specific compounds, complexes, components, ingredients, materials and parts specifically described herein, and may selectively and alternatively exclude any specific compounds, complexes, components, ingredients, materials and parts that are not specifically identified herein as being encompassed by compositions of the invention.

Lewis bases that may be employed in accordance with the present invention to form Lewis base precursor adducts include any suitable Lewis base species, e.g., ethers, glymes, amines, polyamines, etc. Some illustrative polyamines and their abbreviations are follows:

deta=diethylenetriamine;
hmtera=hexamethyltetraethylenepentaamine;
tepa=tetraethylenepentaamine;
pmdeta=pentamethyldiethylenetriamine; and
tmeda=tetramethylethylenediamine.

The precursor compositions of the present invention may be utilized in a liquid delivery MOCVD method of forming a material film on a substrate, comprising the steps of: providing the precursor composition for the material film desired; volatilizing the precursor composition to yield a precursor vapor; and contacting the precursor vapor with the substrate to deposit the material film thereon.

The relative proportions of tetrahydrofuran and the SBT precursor species in respect of one another may be any suitable proportion that produces an SBT film with the desired characteristics when the precursor(s) of interest are dissolved therein and the resultant precursor composition is utilized for liquid delivery MOCVD.

The solvent composition after its formulation may be mixed with the precursor components under gentle mixing, e.g., with a mechanical agitator, inert gas sparger, static mixer, or other mixer device or method, to place the precursor components in solution in the solvent medium, and thereby form the precursor composition, as a source material for liquid delivery MOCVD.

The precursor composition comprising the tetrahydrofuran and the dissolved precursor species therein then can be disposed in a supply vessel or feed liquid reservoir of a liquid delivery MOCVD system for the formation of a material on a substrate in a CVD reactor at suitable process conditions. The process conditions will depend on the specific material being deposited on the substrate, the configuration and geometry of the reactor, the precursor composition employed, and the rate of film growth being effected. The process conditions may readily be determined by suitable empirical approaches without undue experimentation, to determine appropriate temperatures, pressures, flow rates and compositional character of process streams.

The liquid delivery MOCVD system may comprise a system of the type disclosed in U.S. Pat. No. 5,204,314 issued Apr. 20, 1993 to Peter S. Kirlin et al. and in U.S. Pat. No. 5,536,323 issued Jul. 16, 1996 to Peter S. Kirlin et al., which describe heated vaporization structures such as microporous disk elements. In use, liquid source reagent compositions are flowed onto the vaporization structure for flash vaporization. Vapor thereby is produced for transport to the deposition zone, e.g., a CVD reactor. The liquid delivery systems of these patents provide high efficiency generation of vapor from which films may be grown on substrates.

The precursor vapor then is transported to a chemical vapor deposition zone containing a substrate, e.g., a wafer provided on a heated susceptor. Upon contacting of the precursor vapor with the wafer, the metal components of the vapor are deposited on the wafer surface. The vapor may be delivered in the chemical vapor deposition chamber by a disperser such as a showerhead or nozzle, to provide a uniform flux of the vapor across the width of the wafer, to yield a correspondingly uniform thickness of deposited metal-containing film on the wafer. The process conditions (temperature, pressure, flow rate and composition of the vapor) may be suitably controlled to ensure an optimum process result for the MOCVD operation being conducted in the process system.

The liquid delivery process utilizing precursor compositions of the invention to form an SBT material on a substrate therefore includes the steps of:

providing precursor species for the product film to be formed on the substrate and solubilizing same in a solvent comprising tetrahydrofuran according to the invention to form a precursor composition comprising such precursor species and the solvent;

vaporizing the precursor composition to form corresponding precursor vapor; and contacting the precursor vapor with a substrate to deposit the product material thereon.

The advantages of the invention include the following:

(1) the tetrahydrofuran solvent of the invention has increased solubility for the metalorganic precursors that are preferred for the deposition of $SrBi_2Ta_2O_9$ ceramics and derivatives thereof;

(2) the increased solubility allows more robust vaporization, increasing the resistance of the solution to delivery tube clogging within the liquid delivery apparatus;

(3) the increased concentration of metalorganic precursors in the tetrahydrofuran solvent allows for vaporization of the precursors with less heat load from evaporating solvent;

(4) the increased concentration of metalorganic precursor in the tetrahydrofuran solvent increases the growth rate of the film leading to a more manufacturable process; and (5) the increased concentration of metalorganic precursor in the tetrahydrofuran solvent increases the conformality of the films to non-planar structures leading to better performance of the product microelectronic device, e.g., ferroelectric capacitor.

The features and advantages of the invention are more fully shown with reference to the following non-limiting examples.

EXAMPLE 1

Experiments were performed using (1) a baseline 5:4:1 solvent system with a total precursor molarity of 0.20, and (2) a tetrahydrofuran solvent with the concentrations of each metalorganic fixed at the same values with a total solution molarity of 0.3M. The ratios of the different precursors was the same in both systems.

The liquid delivery system used in these experiments was a Sparta™ 450 liquid delivery system (commercially available from Advanced Technology Materials, Inc., Danbury, Conn.) equipped with a ½" vaporizer. The liquid delivery system was attached to a 5" diameter quartz tube reactor as the MOCVD deposition chamber, and such reactor was equipped with temperature controls for independent control of reactor wall temperature and substrate temperature. For films grown in the mass transport limited regime, this reactor enabled growth rates about 3 times greater than the prototype MOCVD reactor mentioned in the Background of the Invention section hereof.

Experiments using 0.2M solution in 5:4:1 solvent showed (1) that the film growth rate was controlled by the rate of delivery of precursor to the surface and (2) that faster precursor delivery to the surface increased conformality.

FIG. 1 shows the growth rate of SBT films as a function of liquid delivery rate for 9 torr processes at 380° C. and 350° C. using 0.2M solution in 5:4:1 octane:decane:pmdeta. Lines indicating a linear proportional increase in growth rate are shown for comparison to the measured increase in growth rate.

Two different growth temperatures were used at a process pressure of 9 torr and 76% $O_2$. At 380° C,. the growth rate increases linearly proportionally with the liquid delivery rate up to 60 mmol/min. The drop-off at 0.5 ml/min is attributed to either the onset of surface reaction limitation or a limitation in the vaporizer's ability to completely vaporize the liquid. At 380° C., the conformality of 1 μm wide by 1 μm deep trenches was 20–30% independent of growth rate.

At 350° C., the growth rate is less than linearly proportional to the liquid delivery rate, but still increases by more than a factor of 2 for a factor of 3 increase in precursor delivery rate. Also, the conformality of the same 1×1 μm trench structures was 30% at 20 mmol/min and 70–80% at 60 mmol/min. This indicates that at the lower temperature, the growth rate becomes dependent upon the surface reaction kinetics in addition to the rate of precursor delivery to the surface, and that as the delivery rate increases, the conformality improves. The data show that there was no growth rate penalty incurred in going to the lower temperature process.

Next, a film was grown with a 0.3M solution in THF. The deposition temperature was 380° C., pressure was 9 torr, the gas was 76% $O_2$, the liquid delivery rate was 0.1 ml/min, and the deposition time was 40 minutes. The film was 290 nm thick and had a composition of $Sr_{0.6}Bi_{2.6}Ta_2O_9$.

Figure 2:
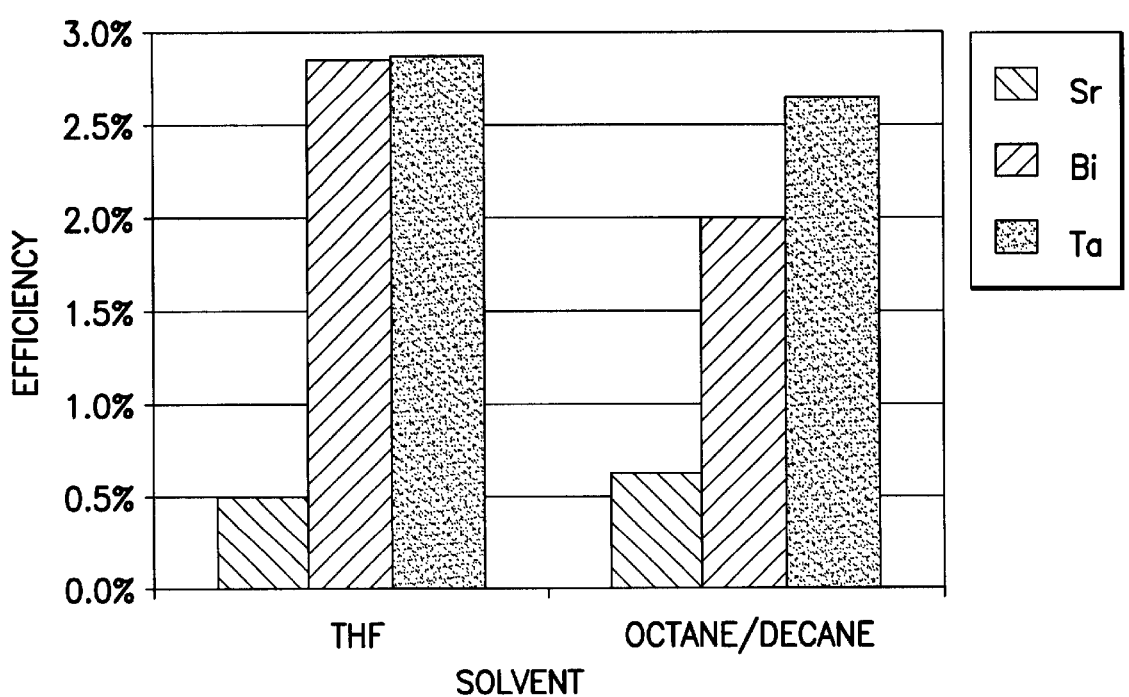
FIG. 2 shows film incorporation efficiency of Sr, Bi and Ta, for a precursor composition using tetrahydrofuran as a solvent and containing the precursors $Sr(thd)_2(THF)_4$ (as a preferred chemical species for the introduction of Sr), $Bi(thd)_3$, and $Ta(O-i-Pr)_4(thd)$, and for a precursor solution of 5:4:1 octane:decane: pmdeta containing the precursors $Sr(thd)_2(pmdeta)$ (as a preferred chemical species for the introduction of Sr), $Bi(thd)_3(pmdeta)$ and $Ta(O-i-Pr)_4(thd)$.

FIG. 2 compares the efficiencies of the individual precursors in this run to those in an equivalent run in the 5:4:1 octane:decane:pmdeta solvent. (Efficiency is defined as the fraction of the precursor delivered to the process that is actually incorporated into the film.) The comparable efficiencies evidence the behavior of the process behaves as being similar to the process with the 5:4:1 octane:decane:pmdeta solvent.

EXAMPLE 2

A tetrahydrofuran solution of $Sr(thd)_2(THF)_4$, $Bi(thd)_3$, and $Ta(O-i-Pr)_4(thd)$ was employed to test vaporizer performance in accordance with the invention, using a liquid delivery MOCVD system of the type described in connection with Example 1, equipped with a ¾" VAPORSOURCE® vaporizer. In this system, argon was employed as a carrier gas, at a flow rate of 300 sccm, a liquid flow rate of 0.3 milliliters per minute was employed, with a total volume of precursor per run, of 50 milliliters. The vaporization elements in the system were stainless steel frits having a pore size of 40 micrometers.

Each experiment was performed by monitoring the pressure above the porous frit element of the vaporizer as a function of time while maintaining the pressure downstream of the frit at 9 Torr using a throttle valve. The pressure above the frit increases as its pores clog with unevaporated precursor residue. Starting with a clean frit element, the rate of pressure rise decreases with time to some "pseudo-steady-state," defined here as the linear pressure rise. After 50 ml of solution have been delivered, the liquid flow is stopped and the pressure above the frit recovers to some steady-state value indicative of the total amount of decomposed precursor in the frit. The pressure rise from the beginning of the run to this final steady-state condition is defined as the net pressure rise.

Large net pressure rise is indicative of decomposed precursor building up in the frit with time. A high rate of linear pressure rise can be the result of unevaporated precursor buildup if it is accompanied by a low pressure recovery. However, if a high rate of linear pressure rise is accompanied by a low pressure recovery, then it is probably indicative of precursor decomposing in the frit before it can be evaporated, which means the vaporization temperature is higher than optimum.

Figure 3:
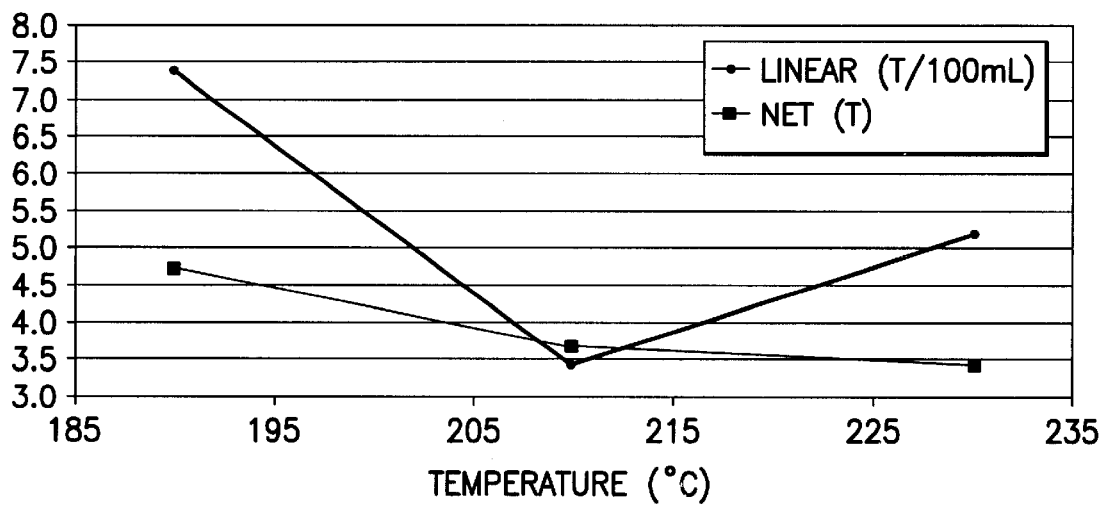
FIG. 3 is a graph of linear and net pressure rises as a function of temperature for a precursor composition using tetrahydrofuran as a solvent and containing the precursors $Sr(thd)_2(THF)_4$ (as a preferred chemical species for the introduction of Sr), $Bi(thd)_3$, and $Ta(O-i-Pr)_4(thd)$, with argon carrier gas.

Linear and net pressure rise was determined as a function of temperature during the runs, generating the data shown in FIG. 3.

FIG. 3 shows a plot of $\Delta P_{linear}$ and $\Delta P_{net}$ as a function of temperature for each of the three runs. Both of these pressure parameters were higher at 190° C. $\Delta P_{linear}$ is the most relevant for predicting vaporizer MTS because it describes long term behavior under steady state conditions, as would be used in a manufacturing environment. Higher pressure rise, along with pressure recovery, indicate that 190° C. may be too low for optimal vaporization of this precursor composition. Over 210–230° C., $\Delta P_{net}$ does not vary much, although the lower value, 3.4 Torr, is at 230° C. Delta $P_{linear}$, however, is minimized at 210° C. (¾ T/100 mL). Under the conditions of this temperature scan, the optimal vaporization was at 210° C., since $\Delta P_{linear}$ appears significantly lower there than at 230° C.

Additional experimentation was carried out with the goal of achieving higher vaporizer on-stream MTS, and for this purpose a temperature scan experiment was designed using a combination of parameters expected to yield higher MTS. Larger frit pore size (100 μm) and a different carrier gas (He) were introduced. A temperature scan was completed under these conditions, again with 20° C. increments, 50 mL total liquid volume, and 300 sccm carrier gas flow rate. A liquid flow rate of 0.2 mL/min was used, consistent with the baseline 5:4:1 octane:decane:pmdeta solvent liquid delivery MOCVD process; the higher solubilities of the precursors in the THF solvent can be used to improve growth rate without increasing liquid flow rate to higher levels.

Figure 4:
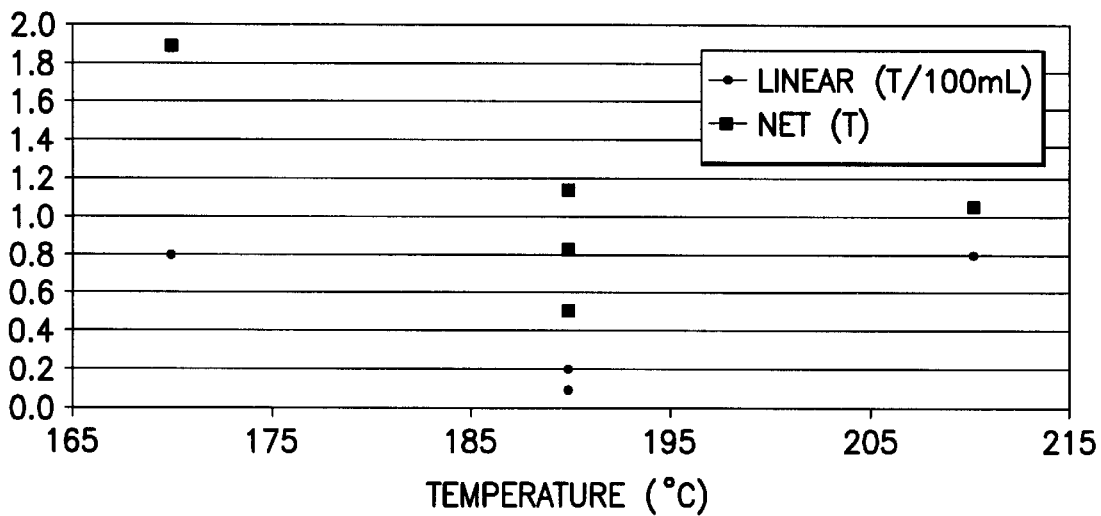
FIG. 4 is a graph of linear and net pressure rises as a function of temperature for a precursor composition using tetrahydrofuran as a solvent and containing the precursors Sr(thd)$_2$(THF)$_4$ (as a preferred chemical species for the introduction of Sr), Bi(thd)$_3$, and Ta(O-i-Pr)$_4$(thd), with helium carrier gas.

A summary of $P_{linear}$ and $\Delta P_{net}$ for the second temperature scan is shown in FIG. 4, which shows linear and net pressure rises as a function of temperature for off-line vaporizer experiments completed with THF solvent system, helium carrier gas at 300 sccm, 100 μm stainless steel frits, a 0.2 mL/min liquid flow rate, and a 50 mL total precursor volume per run. At 210° C., decomposition was observed with $\Delta P_{linear}$ of 0.8 T/100 mL of $\Delta P_{net}$ of 1.1 Torr. At 170° C., recovery was observed with pressure rises of $\Delta P_{linear}$=0.8 Torr/100 mL and $\Delta P_{net}$=1.9 Torr. At the midpoint, 190° C., a pressure rise of $\Delta P_{linear}$32 0.2 T/100 mL and $\Delta P_{net}$=0.5 Torr were observed, and decomposition was noted as the pressure rise mechanism.

The 190° C. condition was replicated to determine repeatability. The first of three runs showed decomposition, the second and third runs at this condition exhibited small pressure recoveries. The $\Delta P_{linear}$ was remarkably consistent over the three runs: 0.1–0.2 torr/100 mL. The $\Delta P_{linear}$ was corrected in one of the runs (run 77) to account for a carrier gas control problem during the second half of the run; this value was measured over 35 mL instead of 50 mL. Both this run and the other (50 ml) runs were extrapolated to 100 mL. The $\Delta P_{net}$ was unaffected.

The $\Delta P_{net}$ varied over 0.1–1.15 Torr. The repeatability range for $\Delta P_{net}$ of this solvent system at this condition measured over 3 runs (0.65 Torr) is similar to that of the octane/decane/pmdeta (5:4:1) solvent system, measured over 6 runs (0.7 Torr).

Figure 5:
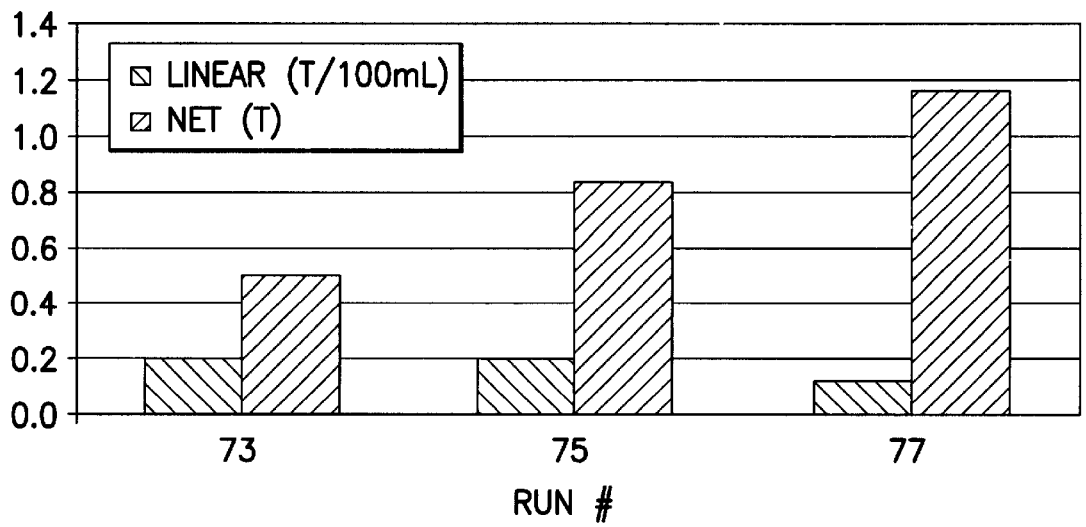
FIG. 5 is a graph of repeatability in terms of linear and net pressure rises for precursor solutions of tetrahydrofuran solvent containing the precursors Sr(thd)$_2$(THF)$_4$ (as a preferred chemical species for the introduction of Sr), Bi(thd)$_3$, and Ta(O-i-Pr)$_4$(thd), in helium carrier gas.

FIG. 5 shows the repeatability for these runs in terms of linear and net pressure rises of 3 runs done with THF solvent system, using 100 μm stainless steel frits, at a 190° C. temperature, with a 300 sccm flow of helium carrier gas, and a 0.2 mL/min liquid flow rate, providing a total volume of 50 mL total precursor per run.

Figure 6:
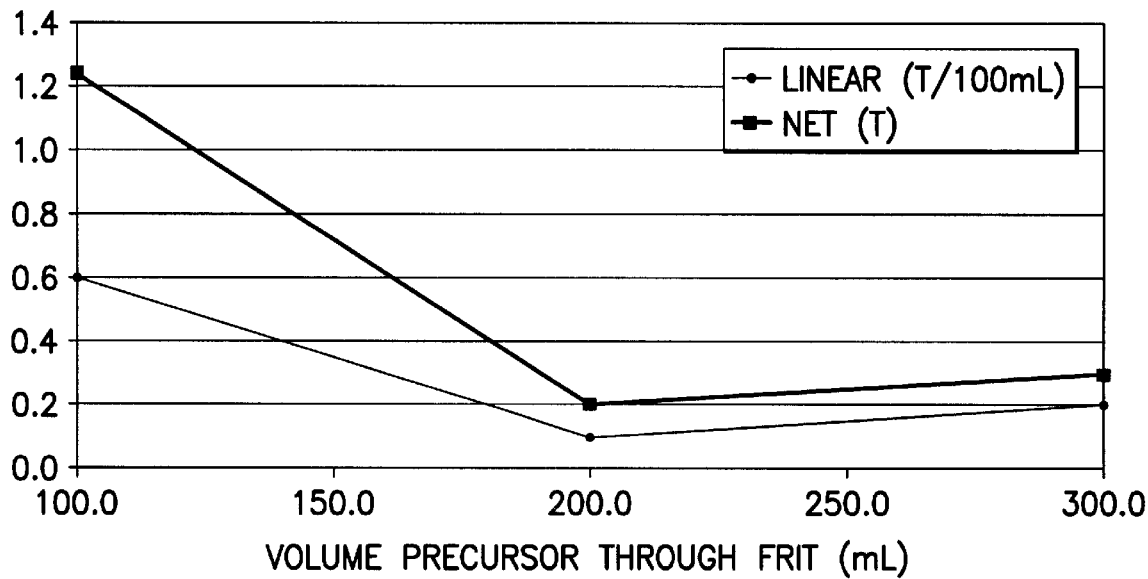
FIG. 6 is a graph of pressure rise as a function of volume of precursor flowed through a frit element for a precursor solution of tetrahydrofuran solvent containing the precursors Sr(thd)$_2$(THF)$_4$ (as a preferred chemical species for the introduction of Sr), Bi(thd)$_3$, and Ta(O-i-Pr)$_4$(thd).

FIG. 6 shows the pressure rise as a function of volume of precursor flowed through one 100 μm stainless steel frit in such system. The THF precursor was flowed in three increments of 100 mL at a temperature of 190° C., a carrier gas flow rate of helium carrier gas of 300 sccm, and a liquid flow rate of 0.2 mL/min for the precursor.

The foregoing results show that significantly improved vaporizer maintenance times were achieved with the tetrahydrofuran-based SBT precursor solutions when using helium as a carrier gas rather than argon, and when using a larger pore size in the porous vaporization element on which the precursor solution is flash vaporized for transport to the CVD reactor. Specifically, the average pore size of the vaporizer element (measured by standard porosimetry techniques) at a value of about 100 micrometers was found to provide significantly better performance than a corresponding vaporizer element having an average pore diameter of about 40 micrometers.

The foregoing results are consistent with the preferred average pore size (diameter) of the vaporization element being in the range of from about 50 to about 200 microns, more preferably in the range of from about 60 to about 120 micrometers, and most preferably in the range of from about 80 to about 110 micrometers. Within these diameter ranges, the viscosity and surface tension (free energy) of the precursor solution are efficiently balanced with the surface area and the capillarity of the porous vaporization element, so that the precursor liquid is quickly thinned and "flash" vaporized as it is applied to the porous vaporization element.

EXAMPLE 3

A precursor solution of 10:1 toluene:pmdeta solvent containing the precursors $Sr(thd)_2(pmdeta)$, $Bi(thd)_3$, and $Ta(O-i-Pr)_4(thd)$ was comparatively tested against a corresponding precursor solution of 5:4:1 octane:decane:pmdeta and a corresponding precursor solution of tetrahydrofuran (THF), using a vaporizer and MOCVD reactor of the type described in Example 1. The ratio of metals in the solution was 43:33:24 Sr:Bi:Ta; the films were deposited in 9 torr of process gas containing 76% $O_2$.

The incorporation efficiency of Sr, Bi and Ta were determined. Efficiency is the fraction of the precursor delivered to the process that is actually incorporated into the product SBT film.

Figure 7:
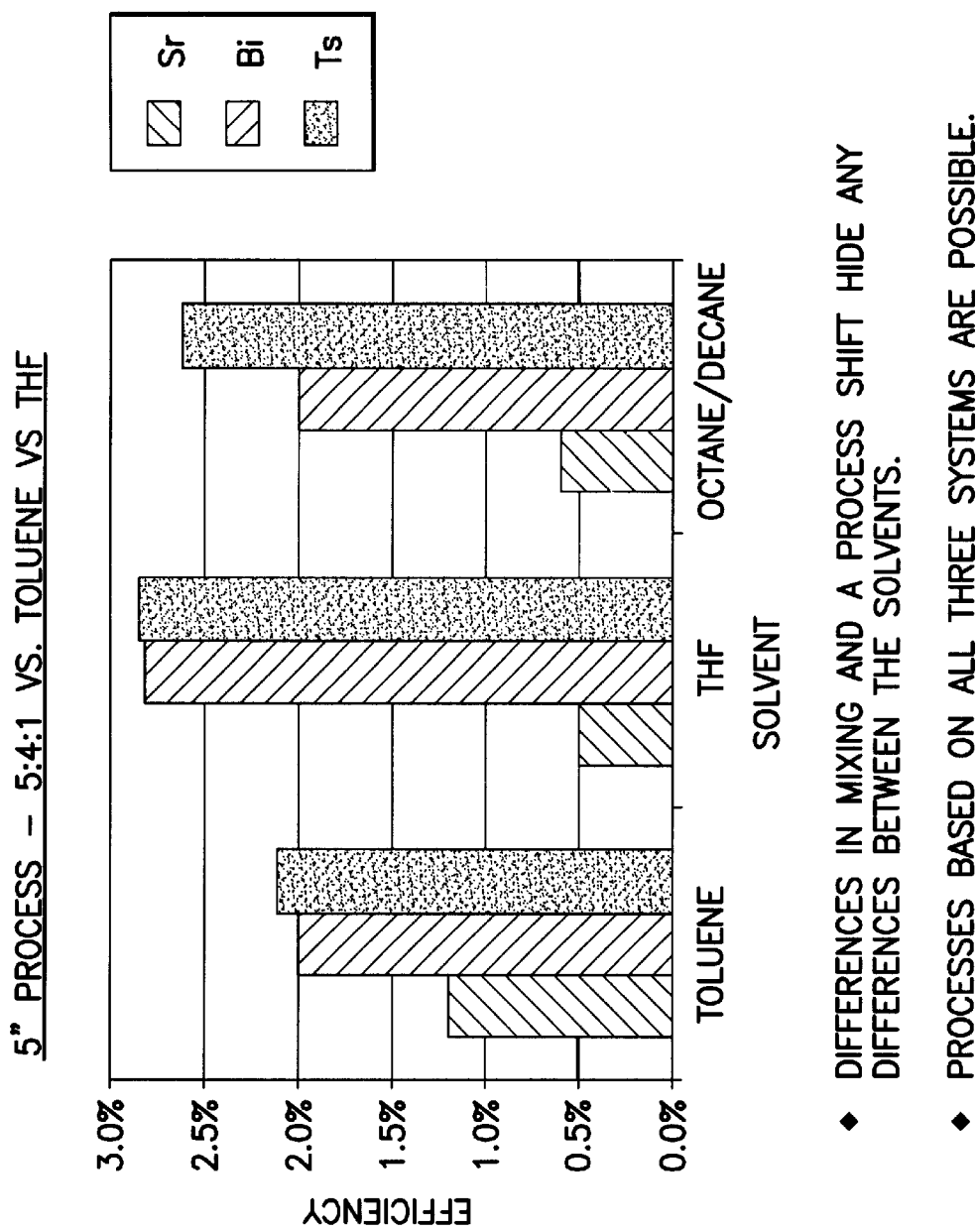
FIG. 7 is a graph of incorporation efficiencies of Sr, Bi and Ta, for (1) a precursor solution of 10:1 toluene: pmdeta solvent containing the precursors Sr(thd)$_2$-LBA (where LBA is pmdeta), Bi(thd)$_3$, and Ta(O-i-Pr)$_4$(thd), (2) a precursor solution of 5:4:1 octane:decane: pmdeta containing the precursors Sr(thd)$_2$-LBA (where LBA is pmdeta), Bi(thd)$_3$, and Ta(O-i-Pr)$_4$(thd), and (3) a precursor solution of tetrahydrofuran (THF), containing the precursors Sr(thd)$_2$-LBA (where LBA is THF), Bi(thd)$_3$, and Ta(O-i-Pr)$_4$(thd).

Efficiencies for the above precursor solutions, as determined, are shown in FIG. 7. These data show similar efficiency of bismuth and tantalum incorporation in the film derived from the precursor solution of THF. Small differences in the resulting films can be corrected by adjusting the precursor mixing ratios.

While the invention has been illustratively described herein with reference to various embodiments and disclosed features, it will be appreciated that the invention is not thus limited, but rather extends to and encompasses numerous variations, modifications and other embodiments. Accordingly, the invention is intended to be broadly construed and interpreted as including all such variations, modifications and other embodiments within the spirit and scope thereof, as hereinafter claimed.

What is claimed is:

1. A precursor composition useful for liquid delivery MOCVD, comprising SBT precursors dissolved in a solvent system consisting essentially of tetrahydrofuran and a Lewis base ligand.

2. The precursor composition of claim 1, wherein said SBT precursors comprise:
   a strontium beta-diketonate;
   a bismuth precursor; and
   a tantalum precursor.

3. The precursor composition of claim 1, wherein the bismuth and tantalum precursors comprise compatible Bi and Ta beta-diketonates.

4. The precursor composition of claim 3, wherein said Sr, Bi and Ta beta-diketonates comprise β-diketonate ligands selected from the group consisting of: acac; hfac; tfac; thd; tod; fod; hfod; and corresponding β-thioketonate ligands.

5. The precursor composition of claim 1, wherein the bismuth precursor comprises a bismuth beta-diketonates.

6. The precursor composition of claim 1, wherein the tantalum precursor comprises a tantalum beta-diketonate.

7. The precursor composition of claim 6, wherein said tantalum beta-diketonate comprises a β-diketonate ligand selected from the group consisting of: acac; hfac; tfac; thd; tod; fod; hfod; and corresponding β-thioketonate ligands.

8. The precursor composition of claim 1, wherein the bismuth precursor comprises a bismuth beta-diketonate coordinated to tetrahydrofuran.

9. The precursor composition of claim 1, wherein said strontium precursor comprises a strontium beta-diketonate.

10. The precursor composition of claim 1, wherein the bismuth precursor comprises $Bi(thd)_3$.

11. The precursor composition of claim 1, wherein the bismuth precursor comprises $Bi(thd)_3$ coordinated to THE.

12. The precursor composition of claim 1, wherein the tantalum precursor comprises $Ta(O-i-Pr)_4(thd)$.

13. The precursor composition of claim 1, having a total solution molarity of from about 0.2M to about 0.6M.

14. The precursor composition of claim 1, further comprising a dopant precursor.

15. The precursor composition of claim 14, wherein the dopant precursor comprises a niobium beta-diketonate.

16. The precursor composition of claim 15, wherein the niobium beta-diketonate comprises $Nb(O-i-Pr)_4(thd)$.

17. The precursor composition of claim 15, wherein said niobium beta-diketonate comprises a β-diketonate ligand selected from the group consisting of: acac; hfac; tfac; thd; tod; fod; hfod; and corresponding β-thioketonate ligands.

18. The precursor composition of claim 14, wherein the precursors comprise $Sr(thd)_2(THF)_4$, $Bi(thd)_3$, $Ta(O-i-Pr)_4(thd)$ and $Nb(O-i-Pr)_4(thd)$.

19. The precursor composition of claim 1, wherein the Lewis base ligand is selected from the group consisting of ethers, glymes, amines and polyamines.

20. The precursor composition of claim 1, wherein the solvent system consists of from about 90 to about 99 parts by volume THF and from about 1 to about 10 parts by volume Lewis base ligand.

21. The precursor composition of claim 1, wherein the SBT precursors comprise $Sr(thd)_2(pmdeta)$, $Bi(thd)_3(pmdeta)$ and $Ta(O-i-Pr)_4(thd)$ and the Lewis base ligand is pmdeta.

22. The precursor composition of claim 21, wherein the solvent system consists of about 90 parts by volume THF and about 10 parts by volume pmdeta.

23. The precursor composition of claim 1 wherein the SBT precursors comprise:
   $Sr(thd)_2(THF)_4$
   $Bi(thd)_3$; and
   $Ta(O-i-Pr)_4(thd)$.

24. A precursor composition useful for liquid delivery MOCVD comprising:
   $Sr(thd)_2(THF)_4$;
   a bismuth precursor; and
   a tantalum precursor,
wherein the precursors are dissolved in a solvent system consisting essentially of tetrahydrofuran.

25. A precursor composition useful for liquid delivery MOCVD comprising:

Sr(thd)$_2$(THF)$_4$;

Bi(thd)$_3$; and

Ta(O-i-Pr)$_4$(thd), wherein the precursors are dissolved in a solvent system consisting essentially of tetrahydrofuran.

26. A method of forming SBT material on a substrate, comprising:

providing a precursor composition for SBT;

volatilizing the precursor composition to yield a precursor vapor; and contacting the precursor vapor with the substrate to deposit SBT thereon;

wherein the precursor composition comprises a strontium beta-diketonate precursor coordinated to tetrahydrofuran, a bismuth precursor, and a tantalum precursor, and wherein the precursors are dissolved in a solvent system consisting essentially of tetrahydrofuran and a Lewis bases ligand.

27. The method of claim 26, wherein the bismuth and tantalum precursors are compatible Bi and Ta beta-diketonates.

28. A method of forming an SBT film on a substrate, comprising liquid delivery MOCVD using a precursor composition comprising a strontium beta-diketonate precursor coordinated to tetrahydrofuran, a bismuth precursor, and a tantalum precursor, wherein the precursors are dissolved in a solvent system consisting essentially of tetrahydrofuran and a Lewis base ligand.

29. The method of claim 28, wherein the bismuth and tantalum precursors comprise compatible Bi and Ta beta-diketonates.

30. The method of claim 29, wherein the Sr, Bi, and Ta beta-diketonate precursors comprise a ligand selected from the group consisting of: acac; hfac; tfac; thd, fod; tod; hfod; and corresponding β-thioketonate ligands.

31. The method of claim 28, wherein the precursor composition includes Sr(thd)$_2$(THF)$_4$, Bi(thd)$_3$, and Ta(O-i-Pr)$_4$(thd).

32. The method of claim 28, having a total solution molarity of the precursor composition of from about 0.2 M to about 0.6 M.

33. The method of claim 28, wherein the precursor composition has a boiling point in the range of from about 60 to about 75° C.

34. The method of claim 28, wherein the precursor composition comprises Sr(thd)$_2$(THF)$_4$.

35. The method of claim 28, wherein the precursor composition comprises Bi(thd)$_3$.

36. The method of claim 28, wherein the precursor composition comprises Ta(O-i-Pr)$_4$(thd).

37. The method of claim 28, wherein the precursor composition comprises a bismuth beta-diketonate coordinated to tetrahydrofuran.

38. The method of claim 28, wherein the precursor composition has a boiling point at 1 atmosphere pressure of about 66° C.

39. The method of claim 28, wherein the precursor composition is volatilized to form a precursor vapor, by contacting a heated porous vaporization element having an average pore size in the range of from about 50 to about 200 microns.

40. The method of claim 28, wherein the precursor composition is volatilized to form a precursor vapor, by contacting a heated porous vaporization element having an average pore size in the range of from about 60 to about 120 microns.

41. The method of claim 28, wherein the precursor composition is volatilized to form a precursor vapor, by contacting a heated porous vaporization element having an average pore size in the range of from about 80 to about 110 microns.

* * * * *